US012256985B2

(12) United States Patent
Zhou et al.

(10) Patent No.: US 12,256,985 B2
(45) Date of Patent: Mar. 25, 2025

(54) MEDICAL DEVICE

(71) Applicant: TERUMO KABUSHIKI KAISHA, Tokyo (JP)

(72) Inventors: Tuo Zhou, Yokohama (JP); Itaru Okubo, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 792 days.

(21) Appl. No.: 17/484,247

(22) Filed: Sep. 24, 2021

(65) Prior Publication Data

US 2022/0008128 A1 Jan. 13, 2022

Related U.S. Application Data

(63) Continuation of application No. PCT/JP2020/011907, filed on Mar. 18, 2020.

(30) Foreign Application Priority Data

Mar. 26, 2019 (JP) .................................. 2019-058929

(51) Int. Cl.
*A61B 18/14* (2006.01)
*A61B 18/00* (2006.01)
(Continued)

(52) U.S. Cl.
CPC ........ *A61B 18/1492* (2013.01); *A61B 2018/00071* (2013.01); *A61B 2018/00077* (2013.01);
(Continued)

(58) Field of Classification Search
CPC ... A61B 18/1492; A61B 18/082; A61B 18/10; A61B 18/12; A61B 18/1206;
(Continued)

(56) References Cited

U.S. PATENT DOCUMENTS 6,123,718 A 9/2000 Tu et al.
6,142,993 A 11/2000 Whayne et al.
(Continued)

FOREIGN PATENT DOCUMENTS

CN 203354638 U 12/2013
JP 2009500052 A 1/2009
(Continued)

OTHER PUBLICATIONS

English Translations of the International Search Report (Form PCT/ISA/210) and the Written Opinion of the International Searching Authority (Form PCT/ISA/237) issued Jun. 23, 2020, by the Japanese Patent Office in corresponding International Application No. PCT/JP2020/011907. (6 pages).

(Continued)

*Primary Examiner* — Thomas A Giuliani
*Assistant Examiner* — Ana Veruska Guerrero
(74) *Attorney, Agent, or Firm* — Buchanan Ingersoll & Rooney PC

(57) ABSTRACT

A medical device capable of improving handling properties and maintaining excellent insulation properties of conductive wires for supplying electricity to electrodes for performing treatment includes: an elongated shaft part having a guide wire lumen formed therein, the guide wire lumen being open at a distal part; a plurality of electrodes which are disposed on the distal side of the shaft part, extend in the longitudinal direction of the shaft part, and are deformable in the radial direction of the shaft part; and a plurality of conductive wires which extend from the proximal side of the shaft part to the distal side thereof and transfer electricity to an electrode layer. The conductive wires extend inside the electrodes and outside the guide wire lumen, and are electrically connected to the electrodes at the distal side of the electrodes.

19 Claims, 5 Drawing Sheets

(51) Int. Cl.
*A61M 25/00* (2006.01)
*A61B 18/08* (2006.01)
*A61B 18/10* (2006.01)
*A61B 18/12* (2006.01)
*A61B 18/24* (2006.01)
*A61M 25/09* (2006.01)
*A61M 25/10* (2013.01)

(52) U.S. Cl.
CPC ............... *A61B 2018/00083* (2013.01); *A61B 2018/0016* (2013.01); *A61B 2018/00172* (2013.01); *A61B 2018/00178* (2013.01); *A61B 2018/00214* (2013.01); *A61B 2018/0022* (2013.01); *A61B 2018/00267* (2013.01); *A61B 2018/00279* (2013.01); *A61B 2018/00285* (2013.01); *A61B 2018/00345* (2013.01); *A61B 2018/00351* (2013.01); *A61B 2018/00369* (2013.01); *A61B 2018/00375* (2013.01); *A61B 2018/00577* (2013.01); *A61B 18/082* (2013.01); *A61B 18/10* (2013.01); *A61B 18/12* (2013.01); *A61B 18/1206* (2013.01); *A61B 18/14* (2013.01); *A61B 18/1402* (2013.01); *A61B 2018/1475* (2013.01); *A61B 18/24* (2013.01); *A61M 2025/0004* (2013.01); *A61M 25/0009* (2013.01); *A61M 25/0012* (2013.01); *A61M 2025/0031* (2013.01); *A61M 25/005* (2013.01); *A61M 25/09* (2013.01); *A61M 2025/09008* (2013.01); *A61M 25/0905* (2013.01); *A61M 25/10* (2013.01); *A61M 25/1018* (2013.01)

(58) Field of Classification Search
CPC ..... A61B 18/14; A61B 18/1402; A61B 18/24; A61B 2018/00071; A61B 2018/00077; A61B 2018/00083; A61B 2018/0016; A61B 2018/00172; A61B 2018/00178; A61B 2018/00214; A61B 2018/0022; A61B 2018/00267; A61B 2018/00279; A61B 2018/00285; A61B 2018/00345; A61B 2018/00351; A61B 2018/00369; A61B 2018/00375; A61B 2018/00577; A61B 2018/1475; A61B 2018/00613; A61M 25/0009; A61M 25/005; A61M 25/09; A61M 25/0905; A61M 25/10; A61M 25/1018; A61M 2025/0004; A61M 2025/0031; A61M 2025/09008

See application file for complete search history.

(56) References Cited

U.S. PATENT DOCUMENTS

| | | | |
|---|---|---|---|
| 6,233,491 B1 * | 5/2001 | Kordis | A61B 18/1492 600/374 |
| 8,103,327 B2 * | 1/2012 | Harlev | A61B 5/283 600/509 |
| 8,128,617 B2 * | 3/2012 | Bencini | A61B 18/02 606/20 |
| 2007/0083194 A1 * | 4/2007 | Kunis | A61B 18/1492 606/41 |
| 2007/0106292 A1 * | 5/2007 | Kaplan | A61F 7/123 606/41 |
| 2013/0172877 A1 * | 7/2013 | Subramaniam | A61B 18/1492 606/41 |
| 2013/0296853 A1 | 11/2013 | Sugimoto et al. | |
| 2015/0045863 A1 * | 2/2015 | Litscher | A61B 18/1492 607/116 |
| 2017/0042615 A1 * | 2/2017 | Salahieh | A61B 5/01 |
| 2018/0184982 A1 | 7/2018 | Basu et al. | |

FOREIGN PATENT DOCUMENTS

| | | |
|---|---|---|
| JP | 2015-112113 A | 6/2015 |
| JP | 2017-143997 A | 8/2017 |
| JP | 2018108376 A | 7/2018 |
| WO | 2018/118798 A1 | 6/2018 |
| WO | 2018/226751 A1 | 12/2018 |

OTHER PUBLICATIONS

The extended European Search Report issued Jun. 9, 2022, by the European Patent Office in corresponding European Patent Application No. 20778797.9—1126. (6 pages).

International Search Report (PCT/ISA/210) with translation and Written Opinion (PCT/ISA/237) mailed on Jun. 23, 2020, by the Japanese Patent Office as the International Searching Authority for International Application No. PCT/JP2020/011907. (8 pages).

Office Action (The First Office Action) issued Apr. 14, 2023, by the National Intellectual Property Administration, P. R. China in corresponding Chinese Patent Application No. 202080023995.7 and an English translation of the Office Action. (12 pages).

* cited by examiner

FIG. 7
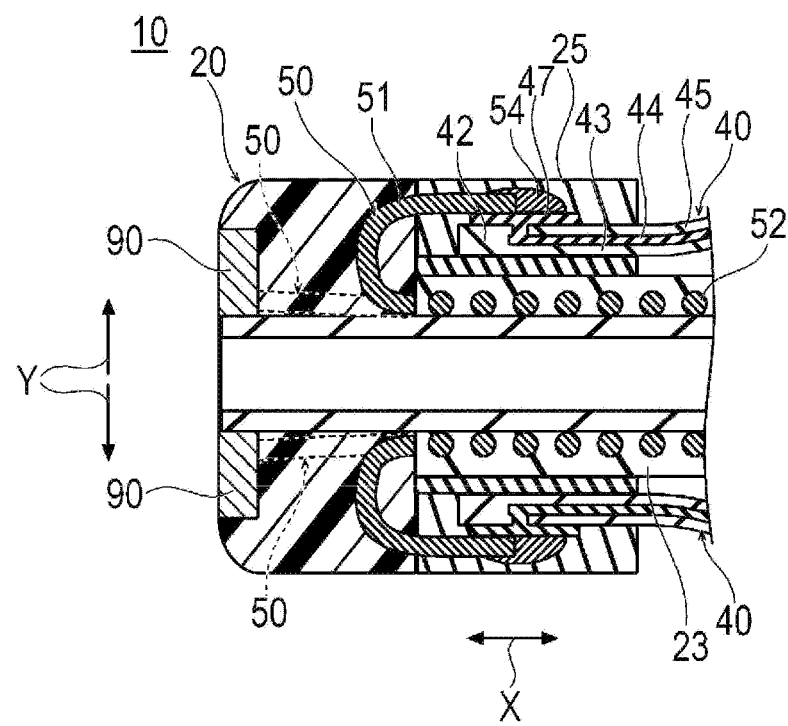
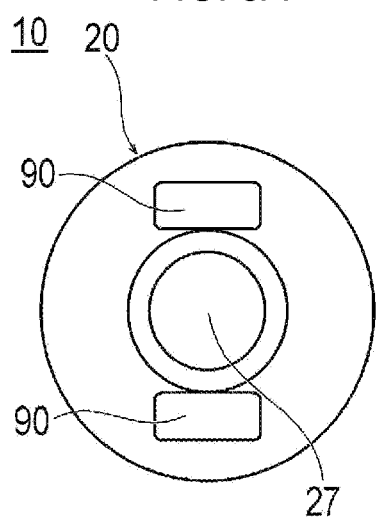
FIG. 8A
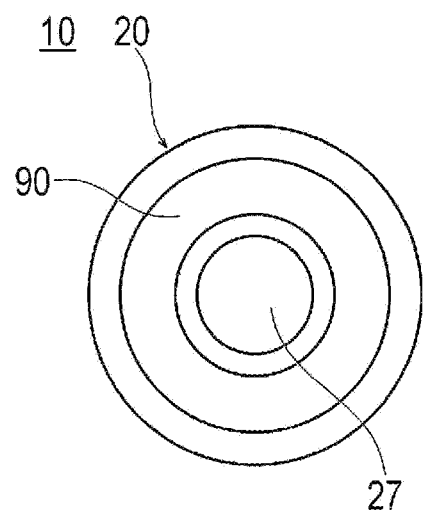
FIG. 8B

MEDICAL DEVICE

CROSS-REFERENCES TO RELATED APPLICATIONS

This application is a continuation of International Patent Application No. PCT/JP2020/011907 filed on Mar. 18, 2020, which claims priority to Japanese Patent Application No. 2019-058929 filed on Mar. 26, 2019, the entire content of both of which is incorporated herein by reference.

TECHNOLOGICAL FIELD

This disclosure generally relates to a medical device that is inserted into an inside of a living body, and performs an electric procedure with respect to a biological tissue.

BACKGROUND DISCUSSION

Medical devices that perform treatment by Irreversible Electroporation (IRE) have been known. Irreversible Electroporation is non-thermal and can suppress damage to blood vessels and nerves in the surrounding. Medical treatment devices that perform treatment using Irreversible Electroporation for cancers difficult to be removed by surgery have been known.

For atrial fibrillation caused by abnormal excitement that occurs in a myocardial sleeve of a pulmonary vein wall, pulmonary vein isolation in which a joint portion between the pulmonary vein and the left atrium is ablated to destroy myocardial cells is performed in some cases. In the pulmonary vein isolation, a high frequency is generated from a tip of an ablation catheter, and cauterize the cardiac muscles in a punctate shape to be necrotized. The ablation catheter is moved so as to circumferentially cauterize the pulmonary vein inflow portion, and isolate the pulmonary vein.

For example, U.S. Pat. No. 6,123,718 describes a device in which electrodes are disposed on an outer peripheral surface of a balloon that is disposed at a distal side of an elongated tubular body. Conductive wires that supply current to the electrodes are disposed in a guide wire lumen of the tubular body at a distal side of the electrodes.

SUMMARY

When the conductive wires are disposed in the guide wire lumen, the motion of a guide wire is hindered by the conductive wires, which results in the reduction in the operability. In addition, a covering layer of the conductive wire may be broken due to friction between the conductive wire and the guide wire, so that there is a possibility that the insulation property of the conductive wire is not maintained. Moreover, when the conductive wire through which electricity is supplied to the electrode is connected to the electrode at the proximal side from the electrode, the outer diameter of the tubular body at the proximal side of the balloon becomes large, and the tubular body at the proximal side of the balloon becomes difficult to bend. When the tubular body is difficult to bend, the operability of the device is lowered.

The medical device disclosed here exhibits improved operability, and is capable of excellently maintaining the insulation property of conductive wires through which electricity is supplied to electrodes that perform treatment.

The medical device disclosed here includes: an elongated shaft portion in which a lumen open in a distal portion thereof is formed; a plurality of electrodes disposed at a distal side of the shaft portion, extend along a long axis direction of the shaft portion, and are deformable in a radial direction of the shaft portion; and a plurality of conductive wires extending from a proximal side to the distal side of the shaft portion, and pass electricity to the electrodes, in which the conductive wires run at an inner side of the electrodes and at an outer side of the lumen, and are electrically connected to the electrodes at a distal side of the electrodes.

In the medical device configured as above, the conductive wires run at the outer side in the radial direction from the lumen, whereby an interference with the guide wire is suppressed. Therefore, the operability of the medical device is improved, and the insulation property of the conductive wires can be excellently maintained. Moreover, the conductive wires are connected to the electrodes at the distal side of the electrodes, whereby the shaft portion that is positioned at the proximal side of the electrodes becomes flexible and are likely to bend because the conductive wires are not concentrated. Accordingly, the operability of the medical device is improved.

According to another aspect, a medical device comprises: a longitudinally extending elongated shaft portion configured to be positioned in a living body, a plurality of circumferentially spaced apart electrodes, and a plurality of conductive wires. The elongated shaft portion includes a lumen configured to receive a guide wire, with the lumen extending in an axial direction along at least a distal portion of the elongated shaft portion and terminating at an open distal end at a distal end of the elongated shaft portion. The plurality of electrodes extend in the axial direction at the distal portion of the elongated shaft portion and are configured to be brought into contact with biological tissue in the living body, wherein the plurality of electrodes are positioned radially outwardly of the lumen in the elongated shaft portion and are deformable radially outwardly away from the lumen and radially inwardly toward the lumen. The conductive wires are each connected to a respective one of the plurality of electrodes and are each configured to convey electricity to the respective electrode when the electrode is in contact with the biological tissue in the living body, with each of the plurality of conductive wires including an intermediate portion extending in the axial direction, a distal end portion distal of the intermediate portion and a proximal end portion proximal of the intermediate portion, and wherein the proximal end portion is positioned outside the elongated shaft portion and is connectable to a power source that supplies the electricity to the electrodes. The intermediate portion of each of the plurality of conductive wires is positioned radially outwardly of the lumen in the elongated shaft portion and radially inwardly of the plurality of electrodes. The distal end portion of each of the plurality of conductive wires is connected to the respective electrode at a position radially outwardly of the lumen in the elongated shaft portion.

In accordance with another aspect, a method comprises introducing a medical device into a living body, wherein the medical device includes: an elongated shaft portion having a lumen that communicates with an open distal end of the elongated shaft portion; a plurality of electrodes located at a distal portion of the elongated shaft portion, extending along an axial direction of the elongated shaft portion and being deformable in a radial direction of the elongated shaft portion; and a plurality of conductive wires extending in the axial direction from a proximal side of the shaft portion to a distal side of the shaft portion, with each of the plurality of conductive wires being positioned radially inwardly of the plurality of electrodes and radially outwardly of the lumen, and each of the plurality of conductive wires being electrically connected to a respective one of the electrodes at a distal side of the respective electrode. The method additionally involves advancing the medical device in the living body to position the plurality of electrodes in contact with biological tissue in the living body, and conveying electricity to the plurality of electrodes by way of the plurality of conductive wires while the electrodes are in contact with the biological tissue in the living body.

BRIEF DESCRIPTION OF THE DRAWINGS

FIG. 4A is a cross-sectional view along the section line 4A-4A in FIG. 2; and FIG. 4B is a cross-sectional view along the section line 4B-4B in FIG. 2.

FIG. 6A illustrates a first modification example, and FIG. 6B illustrates a second modification example.

FIG. 7 is a cross-sectional view illustrating an enlarged distal portion of a medical device in a third modification example.

FIGS. 8A and 8B are plan views respectively illustrating distal end surfaces of medical devices in modification examples: FIG. 8A illustrates the third modification example, and FIG. 8B illustrates a fourth modification example.

DETAILED DESCRIPTION

Figure 1:
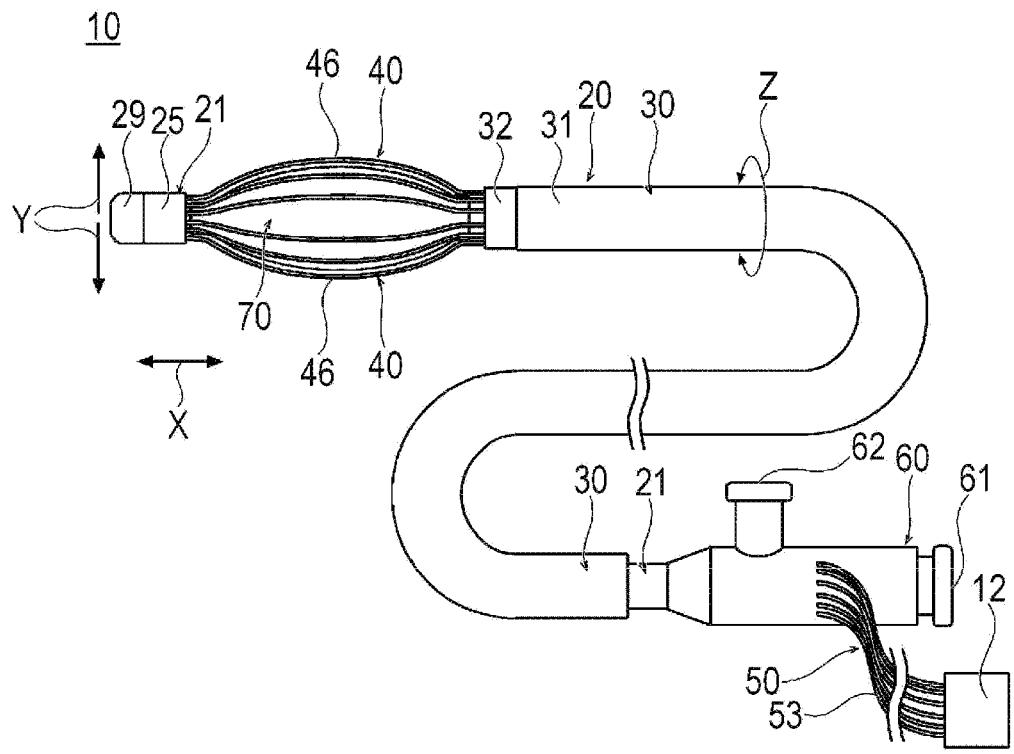
FIG. 1 is a front view illustrating a medical device according to an embodiment.

Set forth below with reference to the accompanying drawings is a detailed description of embodiments of a medical device that is to be inserted into a living body to perform an electric procedure with respect to a biological tissue and that represents examples of the inventive medical device disclosed here. The dimensions on the drawings may be exaggerated or different from the actual dimensions for convenience of description and illustration. Moreover, in the following description and in the drawings, features or components having substantially the same functions are identified by common reference numerals, and a detailed description of features/components already described is not repeated. In the present description, a side of a device to be inserted into the lumen is referred to as a "distal side", and a hand-side where the device is operated is referred to as a "proximal side".

A medical device 10 according to the present embodiment is percutaneously inserted into a lumen of a living body to come into contact with a biological tissue of a target site and apply an electric signal thereto, and conducts Irreversible Electroporation. The medical device 10 according to the present embodiment targets on treatment of electroporation over an entire circumference of an inlet part of a pulmonary vein in the pulmonary vein isolation. Further, the medical device 10 is also applicable to other treatments.

Figure 2:
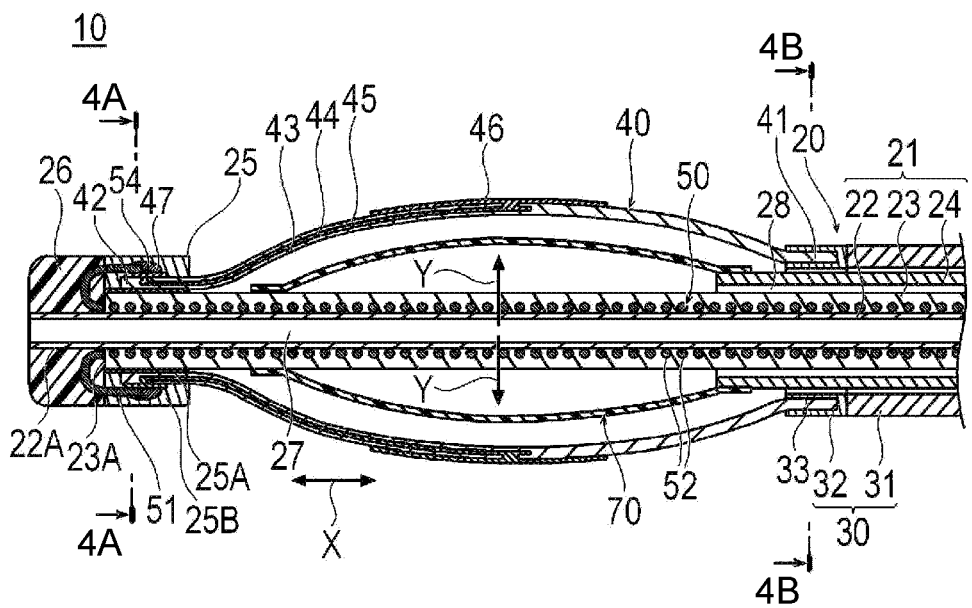
FIG. 2 is a cross-sectional view illustrating a distal portion of the medical device.
Figure 3:
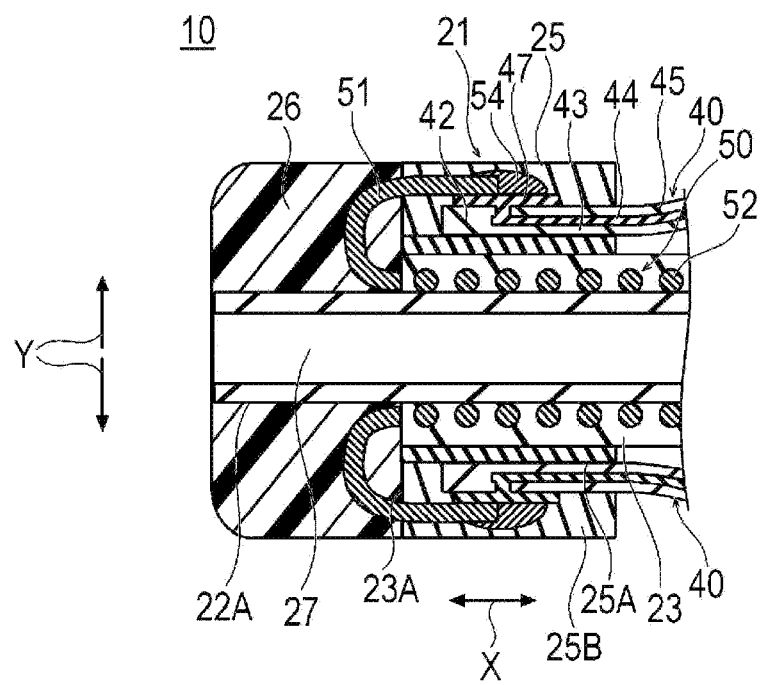
FIG. 3 is a cross-sectional view illustrating the enlarged distal portion of the medical device.

As illustrated in FIGS. 1 to 3, the medical device 10 includes an elongated shaft portion 20, a balloon 70 (inflation body or inflatable body) that is provided at a distal portion of the shaft portion 20, and a hub 60 that is provided at a proximal portion of the shaft portion 20. In addition, the medical device 10 includes a plurality of electrodes 40 that are positioned in surrounding relation to the balloon 70, and conductive wires 50 that transmit current to the electrodes 40.

The shaft portion 20 includes an outer tube 30, and an inner tube 21 that is disposed at an inner side of the outer tube 30. That is, the inner tube 21 is positioned inside the outer tube 30. The outer tube 30 and the inner tube 21 are coaxially disposed. The outer tube 30 and the inner tube 21 are relatively movable in a longitudinal axis direction (axial direction) X of the shaft portion 20.

The outer tube 30 includes a tubular outer tube main body 31, and an annular first support 32 that is fixed to a distal portion of the outer tube main body 31. The first support 32 is an insulative (insulated) member that fixes proximal portions of the electrodes 40 to the outer tube main body 31, as illustrated in FIG. 4B. In the first support 32, a plurality of fixing holes 33 into which the proximal portions of the respective electrodes 40 are inserted from the distal side are formed. The number of the fixing holes 33 coincides with or is equal to the number of the electrodes 40, and the fixing holes 33 are evenly disposed in a circumferential direction of the first support 32. The first support 32 causes the proximal portions of the electrodes 40 to be disposed evenly in a circumferential direction of the outer tube 30 and at suitable inclination to the longitudinal axis direction X.

The inner tube 21 extends to the more distal side than a distal end of the outer tube 30, as illustrated in FIG. 2. That is, distal end of the inner tube 21 extends distally beyond the distal end of the outer tube 30. The inner tube 21 includes a first tubular body 22, a second tubular body 23 that covers an outer peripheral surface of the first tubular body 22 and is fixed to the first tubular body 22, a third tubular body 24 that covers an outer peripheral surface of the second tubular body 23, a second support 25, and a distal tip 26. The conductive wires 50 are disposed between the first tubular body 22 and the second tubular body 23 so as to be sandwiched therebetween. The first tubular body 22 and the second tubular body 23 are coaxially disposed. The first tubular body 22 includes a step portion 22A that extends to the more distal side than a distal end surface 23A of the second tubular body 23. The step portion 22A has a circular tubular shape. A guide wire lumen 27 is formed in an inside of the first tubular body 22. As illustrated in FIGS. 2 and 3, the lumen 27 extends in an axial direction and terminates at an open distal end at the distal end of the elongated shaft portion. A guide wire is insertable into the guide wire lumen 27.

Figure 4A:
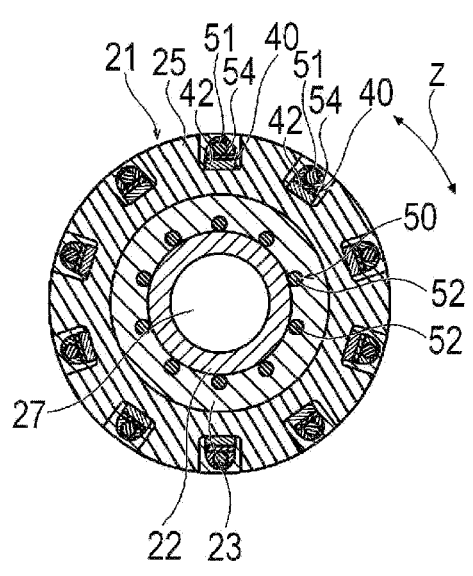
FIGS. 4A and 4B are views illustrating the medical device.
Figure 4B:
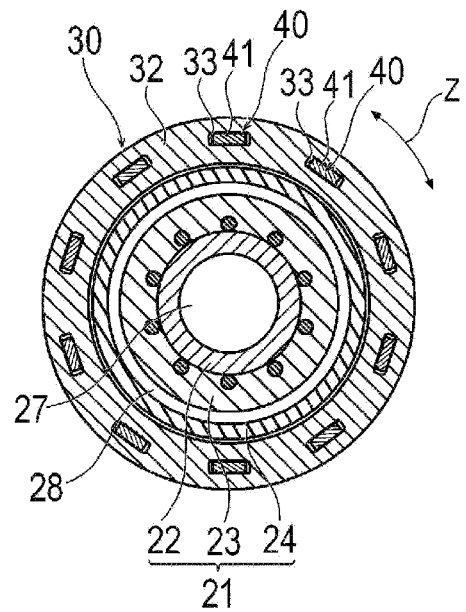

The second support 25 is fixed to an outer peripheral surface of a distal portion of the second tubular body 23, as illustrated in FIGS. 3 and 4A. The second support 25 is an insulative (insulated) member that fixes distal portions of the electrodes 40 to the second tubular body 23. In the second support 25, a plurality of concave-shaped containing units 25A into which the distal portions of the respective electrodes 40 are inserted or positioned from the proximal side (proximal side of the second support 25) are formed. Disposed inside the containing unit 25A are the distal portion of the electrode 40, the conductive wire 50 that is fixed to the electrode 40, and an insulative filling member 25B that fixes the electrode 40 and the conductive wires 50 in a state of being connected to each. The filling member 25B is formed, for example, by a high insulative resin or an adhesive. The second support 25 and the filling member 25B suppress leakage or short circuit of the current from the conductive wires 50 and the electrodes 40. The number of the containing units 25A coincides with (i.e., is equal to) the number of electrodes 40, and the containing units 25A are evenly disposed in a circumferential direction of the second support 25. The second support 25 causes the distal portions of the electrodes 40 to be disposed evenly in a circumferential direction of the inner tube 21 and at suitable inclination relative to the longitudinal axis direction X.

A distal end of the third tubular body 24 is disposed at the more proximal side than a distal end of the second tubular body 23, and disposed at the more distal side than the distal end of the outer tube 30, as illustrated in FIG. 2. That is, the distal end of the third tubular body 24 is proximal of the distal end of the second tubular body 23 and is distal of the distal end of the outer tube 30. An inflation lumen 28 is formed in an outside of the second tubular body 23 and in an inside of the third tubular body 24. An inflating fluid for inflating the balloon 70 can circulate through the inflation lumen 28. The inflating fluid may be gas or a liquid, and for example, the gas such as a helium gas, a $CO_2$ gas, an $O_2$ gas, and laughing gas, and the liquid such as a physiological salt solution, a contrast agent, and an admixture thereof can be used.

The outer diameter of the shaft portion 20 is not specially limited, but is preferably not too large so as to be minimally invasive, and satisfy compatibility with a general sheath or guiding catheter to be inserted, for example, within 5.0 mm, preferably within 3.6 mm.

Constituent materials for fabricating the outer tube main body 31, the first tubular body 22, the second tubular body 23, and the third tubular body 24 preferably have flexibility to some extent. Moreover, the constituent materials for the outer tube main body 31, the first tubular body 22, the second tubular body 23, and the third tubular body 24 preferably have an insulation property. Examples of such the materials can include a polyolefin such as polyethylene, polypropylene, polybutene, an ethylene-propylene copolymer, an ethylene-vinyl acetate copolymer, an ionomer, or a mixture of two or more of them, soft polyvinyl chloride resin, fluorine resin such as polyamide, a polyamide elastomer, polyimide, polyester, a polyester elastomer, polyurethane, or polytetrafluoroethylene, silicone rubber, and latex rubber.

Constituent materials for fabricating the first support 32, and the second support 25 preferably have rigidity to some extent, and preferably have an insulation property. Examples of such the materials can include ceramic, polyphenylene sulfide, and polyimide.

The distal tip 26 is a member that is positioned at a distal end of the inner tube 21, and covers the step portion 22A of the first tubular body 22. The distal tip 26 covers the conductive wires 50 that protrude from the second tubular body 23 to the distal side, and suppresses leakage and short circuit of the currents from the conductive wires 50. A constituent material for fabricating the distal tip 26 preferably has flexibility and an insulation property so as to suppress damage of a tissue in contact with the distal tip 26. Examples of such the material can include polyamide. The distal tip 26 may cover the second support 25.

The balloon 70 is flexibly deformable. In a cross section passing through a longitudinal axis of the shaft portion 20, the shape of the balloon 70 is not specially limited, and is, for example, an approximate cylinder, an approximate ellipse, an approximate trapezoid, or the like. A distal portion of the balloon 70 is fixed to an outer peripheral surface of the distal portion of the second tubular body 23, which is at the more proximal side than the second support 25. That is, as shown in FIG. 2, the distal portion of the balloon 70 is fixed to the outer peripheral surface of the distal portion of the second tubular body 23 at a location that is proximal of the second support 25. A proximal portion of the balloon 70 is fixed to an outer peripheral surface of a distal portion of the third tubular body 24. The balloon 70 has a thin-film shape, and preferably is flexible. Moreover, the balloon 70 is required to have a strength sufficient to reliably expand the electrodes 40. As for constituent materials from which the balloon 70 may be fabricated, the constituent materials for the shaft portion 20 listed above can be used, and constituent materials other than those (for example, various kinds of elastomer raw materials such as a hydrogenated styrenic thermoplastic elastomer (SEBS)) can also be used. The balloon 70 may be a semi-compliant balloon having the comparatively high compliance property, or may be a non-compliant balloon having the comparatively low compliance property. The compliance property is an inflation rate in a radial direction with respect to an inflation pressure to be applied to the balloon 70.

The respective electrodes 40 extend in the longitudinal axis direction (axial direction) X of the shaft portion 20 and have an approximately constant width and thickness, as illustrated in FIGS. 2 and 3. The electrode 40 is formed of a flexible printed circuit, for example. The respective electrodes 40 have flexibility. The respective electrodes 40 are positioned at an outer side in a radial direction Y of the shaft portion 20 relative to the balloon 70, and are not fixed to the balloon 70. The outer side in the radial direction Y is a direction away from the axial center of the shaft portion 20, and an inner side in the radial direction Y is a direction towards the axial center of the shaft portion 20. The electrodes 40 may be partially fixed to the balloon 70. The plurality of electrodes 40 are disposed at the outer side in the radial direction Y relative to the balloon 70 by being arranged or spaced apart in a circumferential direction Z of the shaft portion 20.

Each of the electrodes 40 includes a proximal fixing portion 41 that is positioned at the proximal side, and a distal fixing portion 42 that is positioned at the distal side. The proximal fixing portion 41 is inserted into or positioned in the fixing hole 33 of the first support 32 that is disposed to the outer tube 30, and is fixed by an adhesive and the like. The distal fixing portion 42 is contained in the containing unit 25A of the second support 25 that is disposed to the inner tube 21, and is fixed by the insulative filling member 25B. The proximal fixing portion 41 and the distal fixing portion 42 move closer to or separate from each other along the longitudinal axis direction X, so that a site that is positioned between the proximal fixing portion 41 and the distal fixing portion 42 of the electrode 40 inflates or deflates so as to warp (bend or curve) toward the outer side in the radial direction Y of the shaft portion 20.

Each of the respective electrodes 40 includes a substrate layer 43, a conductive layer 44, an insulating layer 45, an electrode layer 46, and an electric connection portion 47. The substrate layer 43 is an insulative (insulated) layer that is positioned at the inner side in the radial direction Y of the electrode 40. That is, the substrate layer 43 is radially inwardly of the electrode 40. The substrate layer 43 is a layer serving as a foundation on which another layer is adhered. The substrate layer 43 is disposed entirely from the distal end to the proximal end of the electrode 40, meaning the substrate layer 43 extends the entirety of the longitudinal extent of the electrode 40. The conductive layer 44 is a layer having conductivity that is positioned at the outer side of the substrate layer 43 in the radial direction Y (i.e., the conductive layer 44 is radially outwardly of the substrate layer 43). The conductive layer 44 extends from the vicinity of the site (place) where the electric connection portion 47 of the electrode 40 is disposed to the vicinity of the site (place) where the electrode layer 46 of the electrode 40 is disposed. The conductive layer 44 functions as wiring that electrically connects the electric connection portion 47 to the electrode layer 46. The insulating layer 45 is an insulative (insulating) layer that covers the conductive layer 44 on the outer side in the radial direction Y. The insulating layer 45 is thus radially outwardly of the conductive layer 44. An adhesion layer may be provided between the substrate layer 43 and the conductive layer 44, and an adhesion layer may be provided between the conductive layer 44 and the insulating layer 45. The width of the conductive layer 44 is less than the width of the substrate layer 43 and the width of the insulating layer 45. Accordingly, the conductive layer 44 is entirely covered by the substrate layer 43 and the insulating layer 45, and is appropriately insulated from the outside. The width direction of the electrode 40 is a direction orthogonal to the elongated direction and the thickness direction of the electrode 40. The thickness direction of the electrode 40 is a direction in which the substrate layer 43, the conductive layer 44, the insulating layer 45, and the electrode layer 46 are laminated or positioned in overlying relation to one another. That is, the thickness direction of the electrode 40 is the vertical/up-down direction in FIG. 2. The electrode 40 has a dimension greater in the width direction than in the thickness direction.

Figure 5:
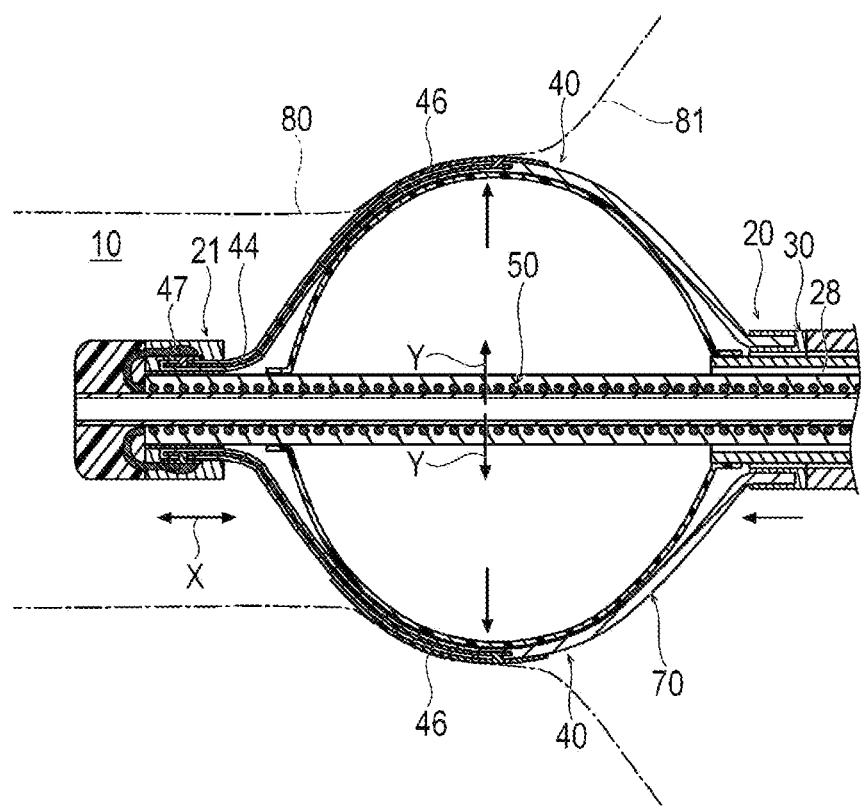
FIG. 5 is a cross-sectional view illustrating the distal portion of the medical device in a state where electrodes are inflated.

The electrode layer 46 is positioned at the outer side in the radial direction Y relative to a site at the more distal side than a central portion and/or an approximate central portion of the balloon 70, when the balloon 70 is inflated (see FIG. 5). That is, when the balloon 70 is inflated, the electrode layer 46 is positioned radially outwardly of: i) portions of the balloon 70 that are distal of the central portion of the balloon; and/or ii) an approximate central portion of the balloon 70. The electrode layer 46 is electrically connected to the conductive layer 44 by penetrating through the insulating layer 45.

The electrode layer 46 is a layer having conductivity that is positioned at the outer side of the insulating layer 45 in the radial direction Y. An adhesion layer may be provided between the electrode layer 46 and the insulating layer 45. Also, the electrode layer 46 may be a part of the conductive layer 44. For example, the insulating layer 45 that covers the conductive layer 44 may be partially removed, and the conductive layer 44 that is exposed to the outside may serve as the electrode layer 46.

The electric connection portion 47 is disposed at a radially outer side of the distal portion of the electrode 40. The electric connection portion 47 is electrically connected to the conductive layer 44 by penetrating through the insulating layer 45.

The electric connection portion 47 is a layer having conductivity that is positioned at the outer side of the insulating layer 45 in the radial direction Y. An adhesion layer may be provided between the electric connection portion 47 and the insulating layer 45. Also, the electric connection portion 47 may be a part of the conductive layer 44. For example, the insulating layer 45 that covers the conductive layer 44 may be partially removed, and the conductive layer 44 that is exposed to the outside may serve as the electric connection portion 47.

The width of the electrode 40 is not specially limited, and may be 0.2 to 2.0 mm, for example. The thickness of the electrode 40 is not specially limited, and may be 0.05 to 1.0 mm, for example. The length of the electrode layer 46 along the elongated direction of the electrode 40 is not specially limited, and may be 1 to 20 mm, for example. The width of the electrode layer 46 is not specially limited, and may be 0.2 to 2.0 mm, for example.

Constituent materials from which the substrate layer 43 and the insulating layer 45 may be fabricated are not specially limited as long as they have flexibility, and a resin material such as polyimide or polyester can be used suitably, for example. Constituent materials from which the conductive layer 44 and the electrode layer 46 may be fabricated are not specially limited as long as they have conductivity, and copper and the like can be used suitably, for example. A surface of the electrode layer 46 may be coated with a material having the conductivity and the X-ray contrast property. The thickness of a layer to be coated may be 5 to 10 μm, for example. Accordingly, an operator can specify a position of the electrode layer 46 under the X-ray fluoroscopy. Examples of such materials having the conductivity and the X-ray contrast property include gold, platinum, or tungsten.

The electrode 40 is not limited to be configured as the flexible printed circuit as long as it has conductivity and is deformable. Constituent materials for fabricating the electrode 40 may be a superelastic metal material represented by an Ni—Ti alloy, other metal materials, or conductive rubber, for example. The electrode 40 excluding the electrode layer 46 of the material having the conductivity and the site to be served as the electric connection portion 47 is preferably coated with the insulating material.

The ten electrodes 40 are evenly provided (i.e., evenly spaced-apart) in the circumferential direction Z, in the present embodiment. Further, the number of the electrodes 40 may be greater or less than ten. An electric signal is applied between the adjacent electrodes 40, and an electrode (or a counter electrode plate) is disposed outside the body, and the electric signal may be applied between the electrode (or counter electrode plate) outside the body and the electrode 40.

Each of the conductive wires 50 is linear, and includes an embedded portion 52 that is embedded in the inside of the inner tube 21, a distal end portion 51 of the conductive wire that protrudes from the distal end surface 23A of the inner tube 21 to the distal side, and a proximal end portion 53 of the conductive wire that is pulled out from or extends out from the hub 60 at the proximal side, as illustrated in FIGS. 1 to 3 so that the proximal end portion 53 is accessible outside the shaft portion 20. The embedded portion 52 is an intermediate portion of the conductive wire 50 that is sandwiched between the first tubular body 22 and the second tubular body 23. For example, a wire rod serving as the conductive wire 50 is wound around the outer peripheral surface of the first tubular body 22, and the second tubular body 23 is formed by extrusion molding to an outside of the first tubular body 22 with the wound wire rod, whereby the embedded portion 52 can be embedded into the inner tube 21. The embedded portion 52 is preferably covered with the material of the outer tube 30 formed by the insulating material without any gap. Accordingly, electrical short circuit caused by the embedded portions 52 coming into contact with each other can be reliably suppressed. The conductive wires 50 are provided in a number equal to or greater than the number of the electrodes 40.

Accordingly, the conductive wires 50 can transmit independent currents to all the electrodes 40. In the present embodiment, the conductive wires 50 are provided in the same number (for example, ten) as the number of the electrodes 40. The plurality of conductive wires 50 are wound in a spiral structure or pattern of multi-strand winding. The plurality of conductive wires 50 are disposed or spaced apart from one another at equal intervals. Accordingly, the plurality of the conductive wires 50 are not electrically short-circuited, and can transmit independent currents. The plurality of conductive wires 50 may be a part of a braided wire rod.

The conductive wires 50 embedded into the inner tube 21 are thus positioned at the more inner side in the radial direction Y than the electrode layer 46 and at the more outer side in the radial direction Y than the guide wire lumen 27, and extend more distally than the electrode layer 46, as illustrated in FIG. 2. The conductive wires 50 extend more distal than the electrode 40 through the inner side in the radial direction Y of the electrode 40, and are turned back to the proximal side while extending toward the outer side in the radial direction Y. That is, the conductive wires 50 extend distally beyond the distal end of the electrodes 40 while being located radially inwardly of the electrodes 40, and the distal portion of each conductive wire is turned to extend radially outwardly and to then extend in the proximal direction as shown in FIG. 3. The end portion of the turned-back distal end portion 51 of each conductive wire 50 is joined to the respective electric connection portion 47 that is disposed at the outer side in the radial direction Y of the electrode 40, in a joint portion 54. The joint portion 54 may be formed by soldering, for example. As long as the distal end portion 51 of the conductive wire and the electric connection portion 47 are electrically connected and conductive, the joint method for joining the two is not limited, and may be soldering, laser fusion, welding using various kinds of metal brazing, bonding by a conductive adhesive, mechanical interlock by a chuck or the like, for example. Joint methods or joining methods may be employed that do not form a joint portion 154. The electric connection portions 47 are disposed at or in the containing units 25A of the second support 25 to suppress short circuit between the electric connection units 47. The electric connection portion 47 may be positioned distal of the containing unit 25A, or may be positioned proximal of the containing unit 25.

The proximal end conductive wires 53 are pulled out from a proximal portion of the third tubular body 24 to the outside via the hub 60, and are connected to a power source unit 12 that is provided at the outside. The power source unit 12 can supply electricity to the electrodes 40.

Constituent materials from which the conductive wire 50 may be fabricated preferably have high conductivity, and copper, gold, platinum, silver, aluminum, an alloy, or carbon fiber are examples of such constituent materials. A publicly known conductive wire can be used as the conductive wire 50.

The hub 60 is interlocked to a proximal portion of the inner tube 21, as illustrated in FIG. 1. The hub 60 includes a first port 61 having an opening that communicates with the guide wire lumen 27, and a second port 62 having an opening that communicates with the inflation lumen 28.

Next, an action and an effect of the medical device 10 according to the present embodiment will be described.

The medical device 10 is moved along a guide wire that is inserted into or positioned in the guide wire lumen 27, and is pushed or moved down into the left atrium from a side of the right atrium. The distal portions of the electrodes 40 in the medical device 10 are inserted into and positioned in an inlet of a pulmonary vein 80 that is a target position, as illustrated in FIG. 5. In other words, the electrodes 40 are introduced from a wider space of the left atrium into a narrower space of the pulmonary vein 80. The electrode layers 46 of the electrodes 40 are disposed in the vicinity of a joint portion 81 between the pulmonary vein 80 and the left atrium. Next, an inflating fluid is supplied into the balloon 70 via the second port 62 and the inflation lumen 28. Accordingly, the balloon 70 inflates or expands radially outwardly, and the electrodes 40 are pushed by the balloon 70 and move to the outer side in the radial direction Y (i.e., move radially outwardly). In this process, the outer tube 30 moves relative to the inner tube 21 in the distal direction, and the proximal portions of the electrodes 40 move to the distal side or in the distal direction. Accordingly, the electrodes 40 can deform while following the inflation of the balloon 70. At least a part of the electrode layers 46 of the electrodes 40 is disposed at an outer side of a site of the balloon 70 the outer diameter of which decreases toward the distal side. Therefore, the electrode layers 46 which are facing in the radially outward direction and in the distal direction are pushed against the pulmonary vein 80 and the joint portion 81 by the balloon 70. The electrode 40 is formed of a flexible printed circuit, so that a failure such as break or short circuit is not so likely to occur in the electrode layer 46, the conductive layer 44, and the electric connection portion 47.

Pulse-like electric signals are applied to the electrode layers 46 of the pair of the electrodes 40 adjacent to each other in the circumferential direction Z of the shaft portion 20 from the power source unit 12 via the conductive wires 50. The electric signals sent from the power source unit 12 are transmitted to the electrode layers 46 of the electrodes 40 via the conductive wires 50, the electric connection portions 47, and the conductive layers 44. Accordingly, a current flows between the pair of the electrodes 40 adjacent to each other in the circumferential direction Z. Next, pulse-like electric signals are applied to another pair of the electrodes 40 adjacent to each other in the circumferential direction Z. The application of the electric signals are successively conducted to all of the pairs of the electrodes 40 adjacent to each other in the circumferential direction Z. The following describes one example of an electric signal to be applied. The electric field strength to be applied by the power source unit 12 is 1500 V/cm, and the pulse width of the electric signal is 100 µsec. The application of electric signals with respect to all of the pair of the electrodes 40 adjacent to each other in the circumferential direction Z is repeated 60 to 180 times in one cycle per two seconds in accordance with a refractory period of the ventricular myocardium. Therefore, cells in the inlet of the pulmonary vein are necrotized over the entire circumference. Note that, electric signals may be applied among the plurality of electrodes 40, which are not adjacent to one another, and an electric signal may be applied to a counter electrode plate attached to a body surface from the electrode 40.

When the balloon 70 is deflated, the electrodes 40 deform or move radially inwardly by their own restoration forces. In this process, the outer tube 30 moves to the proximal side or in the proximal direction with respect to the inner tube 21, and the proximal portions of the electrodes 40 move to the proximal side or in the proximal direction, as illustrated in FIG. 2. Accordingly, the electrode 40 can deform to a shape close to the original straight line while following the deflation of the balloon 70.

The medical device 10 according to the present embodiment includes: the elongated shaft portion 20 in which the guide wire lumen 27 open in a distal portion thereof is formed; the plurality of the electrodes 40 configured to be disposed at a distal side of the shaft portion 20, extend along the long axis direction X of the shaft portion 20, and are deformable in the radial direction Y of the shaft portion 20; and the plurality of the conductive wires 50 configured to extend from a proximal side to the distal side of the shaft portion 20, and pass electricity to the electrode layers 46, in which the conductive wires 50 run at an inner side of the electrodes 40 and at an outer side of the guide wire lumen 27, and are electrically connected to the electrodes 40 at a distal side of the electrodes 40.

In the medical device 10 configured as above, the conductive wires 50 extend or are located more radially outwardly than the guide wire lumen 27, whereby an interference with the guide wire is suppressed. Therefore, the operability of the medical device 10 is improved, and the insulation property of the conductive wires 50 can be excellently maintained. Moreover, the conductive wires 50 are connected to the distal sides of the electrodes 40, whereby the shaft portion 20 that is positioned in the vicinity of the proximal sides of the electrodes 40 become flexible because the conductive wires 50 are not concentrated therein, and are likely to bend. Accordingly, the operability of the medical device 10 is improved. Moreover, the conductive wires 50 are connected to the distal sides of the electrodes 40, whereby the conductive wires 50 hardly move when the electrodes 40 inflate, and the operability is improved. Moreover, the conductive wires 50 are connected to the distal sides of the electrodes 40, whereby the role concentrated on the proximal sides of the electrodes 40 can be dispersed to reduce the diameter of the shaft portion 20.

Moreover, the conductive wires 50 include the embedded portion 52 to be embedded into the shaft portion 20. Accordingly, the conductive wires 50 are not so likely to interfere with other sites, whereby the operability of the medical device 10 is improved. Moreover, the conductive wire 50 is protected by the insulative first tubular body 22 and second tubular body 23, whereby the insulation property can be excellently maintained.

Moreover, at least a part of the embedded portion 52 is wound around the longitudinal axis of the shaft portion 20 in a spiral shape. Accordingly, the shaft portion 20 is reinforced by the conductive wires 50 and is difficult to kink, whereby the operability of the medical device 10 is improved.

Moreover, the conductive wires 50 extend more distally than the electrode 40 by passing through a region or location that is more inwardly than the electrode 40, and the conductive wires 50 are turned back at a location more distal than the electrodes 40 and are connected to the respective electrode 40. Accordingly, the conductive wire 50 can be connected to a position where the electrode 40 can easily access, whereby the manufacturing is easy. Moreover, the distal portion of each electrode 40 to which the respective conductive wire 50 is connected does not need processing such as forming a hole, and thus can be shortened in the longitudinal axis direction (axial direction) X of the shaft portion 20. Therefore, the length of the shaft portion 20 that protrudes more distally than the electrodes 40 can be shortened, whereby the operability of the medical device 10 is improved. The turned-back conductive wires 50 may be connected to a distal end surface of the respective electrode 40 or an inner surface of the respective electrode 40.

Moreover, the turned-back conductive wires 50 are connected to an outer surface of the electrode 40. Accordingly, the conductive wires 50 can be connected to a position at the outer side of the respective electrode 40 where the electrode 40 can be easily accessed, whereby manufacturing is easy.

Moreover, the medical device 10 includes the annular second support 25 that is disposed at an outer peripheral surface of the shaft portion 20, and the second support 25 includes the containing units 25A that contain the distal portions of the electrodes 40. Accordingly, the distal portions of the electrodes 40 are disposed to suitable positions in a circumferential direction of the shaft portion 20. Therefore, the distal portions of the electrodes 40 are disposed at a suitable distance, whereby short circuit of the electrodes 40 and the conductive wires 50 to be connected to the electrodes 40 can be suppressed.

Moreover, the medical device 10 includes the balloon 70 (inflation body) that is disposed between the shaft portion 20 and the electrodes 40. Accordingly, the balloon 70 can effectively push the electrodes 40 against a target site. Accordingly, treatment for a tissue by the electrodes 40 can be effectively performed. Moreover, the balloon 70 is provided and so the shaft portion 20 that is positioned at the more proximal side than the balloon 70 is likely to become thick in order to form the inflation lumen 28 so that the balloon 70 can be inflated. However, in the present embodiment, sites (the electric connection portions 47) at which the conductive wires 50 of the electrodes 40 are connected are disposed at the distal side of the electrodes 40. This can suppress the shaft portion 20 positioned at the more proximal side than the balloon 70 from becoming too thick by the electric connection portions 47 and the conductive wires 50.

This disclosure is not limited to the above-described embodiment, and various changes by those skilled in the art can be made within the technical scope of this disclosure. For example, the above-described embodiment involves a medical device 10 that is used for a procedure of the pulmonary vein 80, but the medical device 10 may be used for a procedure at other sites, for example, a renal artery, an ascending vena cava, or a ventricle.

Figure 6A:
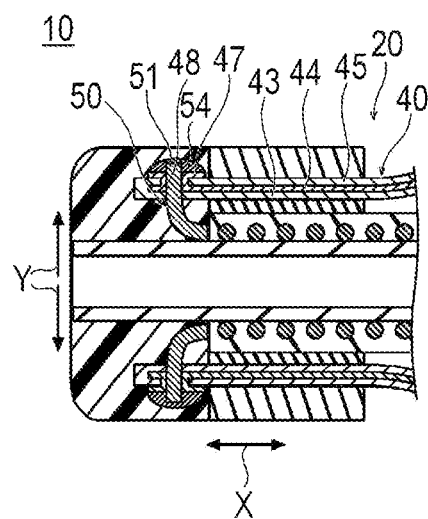
FIGS. 6A and 6B are cross-sectional views respectively illustrating enlarged distal portions of medical devices in modification examples.

According to a first modification example illustrated in FIG. 6A, the electric connection portion 47 of the electrode 40 may be disposed to the outer side in the radial direction Y of the electrode 40, and a through hole 48 extending in the radial direction Y may be formed in the electrode 40 at a site including the electric connection portion 47 or the vicinity of the electric connection portion 47. The conductive wire 50 may be connected to the electric connection portion 47 from the inner side in the radial direction Y of the electrode 40 through the through hole 48. In other words, the radially extending through hole 48 is formed in the electrode 40, and the conductive wire 50 is connected to the electrode 40 by way of this through hole 48. Accordingly, the conductive wire 50 is not required to extend more distal than the electrode 40, whereby the distal portions of the electrodes 40 can be shortened in the longitudinal axis direction X (axial direction). Therefore, the length of the shaft portion 20 that protrudes more distal than the electrodes 40 can be shortened, whereby the operability of the medical device 10 is improved. Moreover, in a state where the conductive wires 50 pass through the respective through hole 48 and the position of the conductive wires 50 is fixed to the electrode 40, the conductive wire 50 can be connected to the electric connection portion 47. Therefore, the workability in the joint is improved. The electric connection portion 47 may be formed by soldering, or by a conductive adhesive, or the like, instead of a configuration of a flexible printed circuit.

For example, melted solder flows into the through holes 48 from the outer side in the radial direction Y, whereby the electric connection portions 47 are formed, and the conductive wires 50 can be electrically connected to the conductive layers 44 in an inside of the through holes 48. The conductive wires 50 may penetrate through the through respective hole 48 from the outer side to the inner side.

Figure 6B:
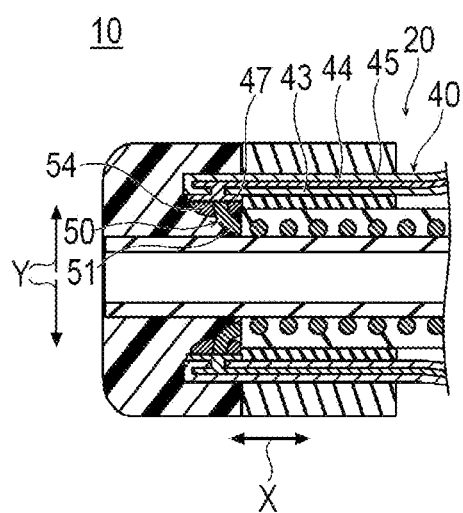

According to a second modification example illustrated in FIG. 6B, the electric connection portion 47 of the electrode 40 is disposed at the inner side in the radial direction Y of the electrode 40, and the conductive wire 50 may be connected to the electric connection portion 47. In other words, each conductive wire 50 is connected to an inner surface of the respective electrode 40. In this case, the distal end portion 51 of each conductive wire is joined to the respective electric connection portion 47 without having to extend from a position at the radially inner side of the electrode 40 to the radially outer side of the electrode. Accordingly, the conductive wire 50 is not required to extend more distal than the electrode 40. In addition, a hole or the like is not required to be formed in the distal portion of the electrode 40 where the electric connection portion 47 is formed. Therefore, the distal portions of the electrodes 40 can be shortened in the longitudinal axis direction (axial direction) X of the shaft portion 20. Accordingly, the length of the shaft portion 20 that protrudes distal of the electrodes 40 can be shortened, whereby the operability of the medical device 10 is improved. Moreover, the joint portion 54 between the electric connection portion 47 and the conductive wire 50 is disposed at the inner side in the radial direction Y of the electrode 40, whereby the outer diameter in the distal portion of the medical device 10 can be suppressed. Therefore, the invasiveness of the medical device 10 can be suppressed.

According to a fourth modification example illustrated in FIGS. 7 and 8A, the medical device 10 may include two second electrodes 90 in a distal end surface of the shaft portion 20. Different conductive wires 50 are electrically joined to the two second electrodes 90. Accordingly, the number of conductive wires 50 is preferably equal to or greater than the total of the number of the electrodes 40 plus the number of second electrodes 90. The plurality of conductive wires 50 connected to the electrodes 40 extend to the distal side of the electrodes 40 so as to be capable of joining to the distal portions of the electrodes 40. Therefore, the two conductive wires 50 are easily guided to the second electrodes 90. The medical device 10 can ablate a tissue by pushing the second electrodes 90 against a place where the ablation by the electrodes 40 is insufficient, for example. When the ablation is conducted by the second electrodes 90, pulse-like electric signals are applied to the two second electrodes 90. One second electrode 90 may be disposed as a fifth modification example illustrated in FIG. 8B. The shape of the second electrode 90 is not specially limited, and is a ring shape or annular shape in the illustrated example. In the fourth modification example, electric signals are applied to the second electrode 90 and a counter electrode plate attached to the body surface, whereby the tissue can be ablated.

Figure 9:
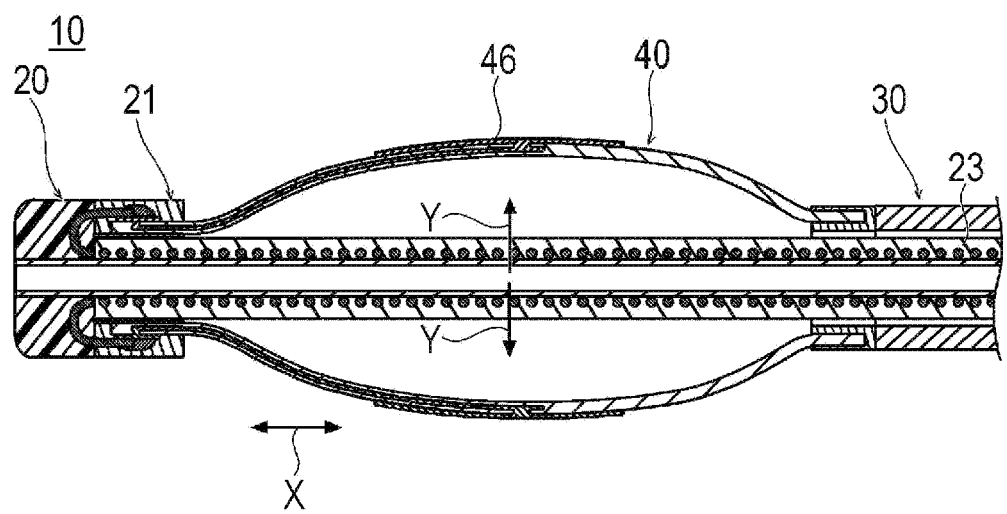
FIG. 9 is a cross-sectional view illustrating a distal portion of a medical device in a fifth modification.

Moreover, as according to a fifth modification example illustrated in FIG. 9, the medical device 10 may include no balloon (inflation body). In this case, in the inner tube 21, the inflation lumen is unnecessary, and the third tubular body 24 (see FIG. 2) at the outer side in the radial direction Y of the second tubular body 23 does not need to be disposed. The medical device 10 can cause the electrodes 40 to deform so as to warp or bend to the outer side and the inner side in the radial direction Y by relatively moving the outer tube 30 and the inner tube 21 in the longitudinal axis direction (axial direction) X of the shaft portion 20, without including the balloon.

Moreover, the conductive wires 50 that transmit the current to the electrode 40 does not need to have a spiral shape nor be a part of the braid wire rod. For example, the conductive wires 50 may be wire rods that linearly extend along the longitudinal axis direction (axial direction) X of the shaft portion 20. Moreover, the conductive wires 50 may be wire rods that are configured to be curved or bent.

Moreover, as long as an extendable site is provided to a part of the electrode 40, the outer tube 30 and the inner tube 21 do not need to be relatively movable in the longitudinal axis direction (axial direction) X. In this case, when the balloon 70 inflates and the electrodes 40 are curved to the outer side in the radial direction Y, the extendable site extends, whereby the outer tube 30 and the inner tube 21 are not required to relatively move.

Moreover, the medical device may be configured so that neither the first support 32 nor the second support 25 is provided.

Moreover, the conductive wires 50 do not need to be embedded in the inner tube 21. Moreover, the outer tube 30 may be provided with no outer tube main body 31, and may only include the first support 32 that can slide in the longitudinal axis direction (axial direction) X with respect to the outer peripheral surface of the inner tube 21.

The detailed description above describes embodiments of a medical device representing examples of the inventive medical device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
    an elongated shaft portion, the elongated shaft portion including a lumen that communicates with an open distal end of the elongated shaft portion;
    a plurality of electrodes disposed at a distal end portion of the elongated shaft portion and extending along a longitudinal axis direction of the elongated shaft portion, the plurality of electrodes being deformable in a radial direction of the elongated shaft portion;
    a plurality of conductive wires configured to convey electricity to the plurality of electrodes, the plurality of conductive wires extending from a proximal side of the shaft portion to a distal side of the elongated shaft portion;
    wherein the elongated shaft portion includes a first tubular body defining the lumen formed inside of the first tubular body, and a second tubular body that covers an outer peripheral surface of the first tubular body, the second tubular body being coaxially disposed at the first tubular body;
    wherein each the plurality of conductive wires includes an embedded portion that is disposed and sandwiched between the first tubular body and the second tubular body;
    wherein the first tubular body, the second tubular body and the embedded portion extend to a distal end portion of the plurality of electrodes at an inner side of the plurality of electrodes and at an outer side of the lumen of the first tubular body, each of the plurality of conductive wires being electrically connected to a respective one of the electrodes at a distal side of the respective electrode.

2. The medical device according to claim 1, wherein at least a part of the embedded portion is wound in a spiral shape around a longitudinal axis of the shaft portion.

3. The medical device according to claim 1, wherein each of the plurality of conductive wires extends to the distal side of the electrodes by extending along at the inner side of the plurality of electrodes and turning back upon itself at a position distal of the plurality of electrodes and connected to the respective electrode.

4. The medical device according to claim 3, wherein each of the plurality of conductive wires is connected to an outer surface of the respective electrode.

5. The medical device according to claim 1, wherein each of the plurality of conductive wires is connected to an inner surface of the respective electrode.

6. The medical device according to claim 1, wherein each of the plurality of electrodes includes a through hole passing through the electrode in the radial direction, and
each of the plurality of conductive wires passes through the through hole in the respective electrode and is connected to the respective electrode.

7. The medical device according to claim 1, further comprising:
an annular support at an outer peripheral surface of the shaft portion, the annular support comprising at least one containing unit that contains a distal portion of one of the plurality of electrodes.

8. The medical device according to claim 1, further comprising:
an inflatable inflation body disposed between the shaft portion and the plurality of electrodes.

9. A medical device comprising:
a longitudinally extending elongated shaft portion configured to be positioned in a living body, the elongated shaft portion including a lumen configured to receive a guide wire, the lumen extending in an axial direction along at least a distal portion of the elongated shaft portion and terminating at an open distal end at a distal end of the elongated shaft portion;
a plurality of circumferentially spaced apart electrodes extending in the axial direction at the distal portion of the elongated shaft portion and configured to be brought into contact with biological tissue in the living body, the plurality of electrodes being positioned radially outwardly of the lumen in the elongated shaft portion and being deformable radially outwardly away from the lumen and radially inwardly toward the lumen;
a plurality of conductive wires each connected to a respective one of the plurality of electrodes and each configured to convey electricity to the respective electrode when the electrode is in contact with the biological tissue in the living body, each of the plurality of conductive wires including an intermediate portion extending in the axial direction, a distal end portion distal of the intermediate portion and a proximal end portion proximal of the intermediate portion, the proximal end portion being positioned outside the elongated shaft portion and being connectable to a power source that supplies the electricity to the electrodes, the intermediate portion of each of the plurality of conductive wires being positioned radially outwardly of the lumen in the elongated shaft portion and radially inwardly of the plurality of electrodes; and
wherein each of the plurality of circumferentially spaced apart electrodes includes:
an electric connection portion that is disposed near a distal end of the medical device, the electric connection portion being connected to the respective distal end portion of the respective conductive wire;
the elongated shaft portion including a first tubular body defining the lumen formed inside of the first tubular body, and a second tubular body that covers an outer peripheral surface of the first tubular body, the second tubular body being coaxially disposed at the first tubular body; and
the intermediate portion of each the plurality of conductive wires extends to the respective distal end portion of the respective conductive wire and is sandwiched between the first tubular body and the second tubular body at an inner side of the plurality of electrodes and at an outer side of the lumen.

10. The medical device according to claim 9, wherein each of the plurality of circumferentially spaced apart electrodes further includes:
a substrate layer that disposed inside a conductive layer in a radial direction of the respective electrode, the substrate layer having insulation; and
an insulating layer that is disposed outside the conductive layer in the radial direction of the respective electrode.

11. The medical device according to claim 9, wherein the elongated shaft portion includes an inner tube positioned inside an outer tube, the inner tube and the outer tube being axially movable relative to one another, each of the plurality of electrodes including one end connected to a first support that is fixed to the outer tube and an opposite end connected to a second support that is fixed to the inner tube.

12. The medical device according to claim 9, wherein the intermediate portion of each of the plurality of conductive wires is a spirally wound intermediate portion that surrounds the lumen in the elongated shaft portion.

13. The medical device according to claim 12, wherein the spirally wound intermediate portion of each of the plurality of conductive wires is embedded in the elongated shaft portion.

14. The medical device according to claim 9, wherein each of the plurality of electrodes includes a distal-most end, the distal end portion of each of the plurality of conductive wires extending distally beyond the distal-most ends of the plurality of electrodes, being bent-back upon itself and being fixed to a radially outwardly facing surface of the respective electric connection portion of each of the plurality of electrodes.

15. The medical device according to claim 9, wherein the distal end portion of each of the plurality of conductive wires is fixed to a radially inwardly facing surface of the respective electric connection portion of each of the plurality of electrodes.

16. The medical device according to claim 9, wherein the distal end portion of each of the plurality of conductive wires passes through a through hole in a distal end portion of the respective electrode and is fixed to a radially outwardly facing surface of the respective electric connection portion of each of the plurality of electrodes.

17. The medical device according to claim 9, wherein the first tubular body and each of the plurality of conductive wires extend distal of the second tubular body, the distal end portion of each of the plurality of conductive wires bends outwardly distal of the second tubular body.

18. The medical device according to claim 9, further comprising an inflatable inflation body disposed between the shaft portion and the plurality of electrodes.

19. The medical device according to claim 1, wherein the first tubular body extends distal of the second tubular body; and each of the plurality of conductive wires includes a distal end portion that extends distal of the second tubular body from the embedded potion, the distal end portion extending distal of the second tubular body from the embedded portion and being bent outwardly.

\* \* \* \* \*